United States Patent [19]
Herman et al.

[11] 4,401,795
[45] Aug. 30, 1983

[54] POLYMERIC POLYELECTROLYTES

[75] Inventors: Daniel F. Herman, Princeton; Uno Kruse, Neptune, both of N.J.

[73] Assignee: NL Industries Inc., New York, N.Y.

[21] Appl. No.: 223,441

[22] Filed: Jan. 8, 1981

Related U.S. Application Data

[62] Division of Ser. No. 56,564, Jul. 11, 1979, abandoned.

[51] Int. Cl.³ .............................................. C08F 20/04
[52] U.S. Cl. .............................. 525/327.8; 525/328.9; 526/272; 526/317; 525/330.2
[58] Field of Search ......................... 526/317; 525/329

[56] References Cited

U.S. PATENT DOCUMENTS

| 3,971,766 | 7/1976 | Ono et al. | 526/317 |
| 4,062,817 | 12/1977 | Westerman | 526/317 |
| 4,071,650 | 1/1978 | Gross | 526/317 |
| 4,138,380 | 2/1979 | Barabas et al. | 526/214 |

Primary Examiner—Harry Wong, Jr.

[57] ABSTRACT

There is provided a polymer useful as a water absorbing agent. The polymer preferably contains the reaction product of an olefinically-unsaturated carboxylic acid, an alkyl acrylate and minor amounts of a crosslinking agent all in specified proportions.

10 Claims, No Drawings

POLYMERIC POLYELECTROLYTES

This is a division of application Ser. No. 56,564, filed July 11, 1979, and now abandoned.

This invention relates to the preparation of polymeric materials, and particularly to solid, water-swellable, water-insoluble polymers which have utility in absorbent articles.

Various systems have been proposed to produce water-swellable, water-insoluble polymeric materials. Such materials have been prepared from carboxyl-containing polymers by polymerization of carboxylic acid monomers in the presence of a crosslinking agent. Such monomers have included acrylic acid, maleic acid, maleic anhydride and the like. Such linear carboxylate polymers include acrylic acid-acrylate copolymers, acrylic acid-acrylamide copolymers, acrylic acid-olefin copolymers. U.S. Pat. No. 3,980,663 discloses producing such polymers by reacting a water-soluble low molecular weight polyelectrolyte which contains nucleophilic carboxyl ions with a crosslinking agent containing two or more sites which are subject to nucleophilic attack by the carboxylate groups. The process is exemplified by the reaction in an aqueous solution of a sodium salt of an acrylic acid-methyl acrylate copolymer (prepared by adding sodium hydroxide to a latex of the copolymer) crosslinked with glycerine diglycidyl ether. The resulting product was cast into a film and cured for one hour in an oven. This process and product, however, have various disadvantages. The crosslinking reaction is slow, requiring special large driers to provide the necessary residence time for curing. In addition, crosslinking is achieved by forming diester bridges between linear polymer chains. Such links are subject to hydrolysis and therefore polymer degradation. A further disadvantage of this patent is the preparation of a film which can only be formed into a particulate material by grinding. This results in a product having a low surface/weight ratio inherent in a film which results in slow water absorption and the tendency for the swollen surface of the film to block the further penetration by water during an absorption test. Thus, the core of the film contributes its swelling capacity only slowly if at all.

Other polymeric systems have also been proposed with the underlying consideration being the formation of a water-swellable, water-insoluble material that is capable of absorbing large amounts of water without disintegrating or being solubilized. It has been noted by Verbrugge in an article entitled "Mechanism of Alkali Thickening of Acid-Containing Emulsion Polymers" reported in the *Journal of Applied Polymer Science*, Vol. 14, pages 897 to 928, 1970, that acid containing latexes during neutralization all undergo a common swelling process leading to complete solubilization for the more hydrophilic polymers. Verbrugge described specific neutralization reactions in a series of polymers of varying Tg and hydrophilicity of the general formula methyl methacrylate/ethyl acrylate/methacrylic acid (MMA/EA/MAA) utilizing 20 mole % of MAA and varying ratios of MMA/EA from 50/0 to 0/80. Observations were made of both viscosity changes and visual changes in a light microscope. Work is also disclosed at the higher hydrophilic range of monomer, e.g., utilizing high EA/MAA contents such as 80/20 and 70/30 EA/MAA with zero MAA. The light microscope shows gradual swelling of the particles at the carboxylic acid groups were progressively neutralized. At 80% neutralization, the particles are disclosed as being so highly swollen as to make the phase change from solid to liquid medium barely distinguishable. At 90% and 100% neutralization, the particles are gone and a true solution is formed. Polymer latex particles which are less hydrophilic, e.g., those observed from high MAA levels and lower EA and MAA, e.g., 60/20/20 MMA/EA/MAA, result in viscous gels upon neutralization and are seen in the light microscope as barely discernable swollen gel particles with no clear boundary between the swollen particle and the solution. Electron microscope examination of the dried 100% neutralized latex particle shows numerous tentacles projecting from the central core which result in association or sticking together of particles which in turn result in high viscosity. Verbrugge then discloses the preparation of four EA/MAA copolymers which are highly cross-lined with ethylene glycol dimethacrylate at 15 and 30% levels. MAA content is 20 and 30%. The latexes prepared at 15% crosslinking swelled upon neutralization and resulted in much higher viscosity than obtained for the uncrosslinked polymer. The 30% crosslinked material because of its extremely high crosslink density shows neither swelling or viscosity.

The present invention is an improvement over the prior art water-swellable, water-insoluble polymers in that it combines specific short chain monomers with minor amounts of a crosslinking agent during polymerization. The resulting polymer when neutralized forms an absorbent product which when swollen forms gelled microspheres having a dry-to-the-touch feel. This coupled with the adsorbents' unusual retention of absorbed fluids makes the absorbent of the invention of substantial importance for all articles of manufacture requiring an absorption capability and, for example, in such diverse articles as spherical and dental sponges, catamenial tampons, diapers, meat trays, paper towels, and disposable litter mats for household pets.

In accordance with the present invention, a polymer has been unexpectedly discovered which comprises (a) from about 15% to about 50% by weight of an olefinically-unsaturated carboxylic acid; (b) from about 49.07% to about 82% by weight of an alkyl acrylate wherein the alkyl group has from 1 to 4 carbon atoms; and (c) from about 0.03% to about 3.0% by weight of a crosslinking agent. All indicated amounts are by weight and based upon the total weight of the components of the polymer.

Also provided is an alkaline salt and organic amine salt of the above-defined polymer which materials are useful as a water absorbing agent. Exemplary alkaline salts may be selected from sodium, potassium, lithium and ammonium. Exemplary organic amine salts may be selected from trimethyl amine and triethanol amine.

In the production of the polymers of this invention, a monomeric mixture which contains an olefinically-unsaturated carboxylic acid and an alkyl acrylate is polymerized in the presence of minor amounts of a vinyl crosslinking agent. Crosslinking is achieved by introducing the vinyl groups of the crosslinking agent directly into the carbon-carbon backbone of the polymer. Where long term resistance to degradation is required, hydrolytically stable crosslinking agents such as divinyl benzene or triallylcyanurate may be employed.

The general structure of the compounds of this invention may be represented as:

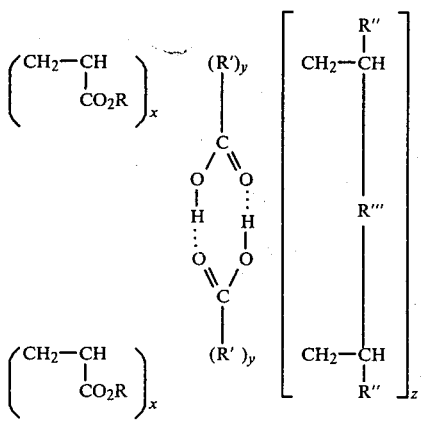

wherein:

x represents the relative number of alkyl acrylate groups with R being 1 to 6 carbon atoms.

y represents the relative number of olefinically-unsaturated carboxylic acid groups with R' being the hydrocarbon portion of the carboxylic acid compounds herein defined containing the olefinic grouping which becomes part of the carbon-carbon backbone.

z represents the relative number of crosslinking agents with R" being hydrogen or methyl and R"' being the remaining portion of the crosslinking agent molecule as herein defined.

While the formula depicted shows a specific arrangement of monomers containing all three groups, it should be recognized that in reality the groups are randomly distributed within the polymer chain.

The olefinically-unsaturated carboxylic acids useful in the invention are those materials containing an activated carbon-to-carbon olefinic double bond and at least one carboxyl group, that is an acid containing an olefinic double bond. Representative examples of suitable carboxylic acids include acrylic acid, methacrylic acid, ethacrylic acid, crotonic acid, muconic acid, aconitic acid and similar compounds as well as mixtures thereof. The preferred carboxylic acids are acrylic acid and methacrylic acid.

The alkyl acrylates useful in the invention are those alkyl acrylates wherein the alkyl group has from 1 to 6 carbon atoms and preferably 1 to 4 carbon atoms. Representative examples of suitable acrylates include methyl acrylate, ethyl acrylate, propyl acrylate, n-butyl acrylate and iso-butyl acrylate. The preferred acrylates are methyl acrylate, ethyl acrylate and n-butyl acrylate with methyl acrylate being most preferred. Higher chained acrylates have a tendency to become hydrophobic causing the final polymer salt to exhibit lower swelling and water absorption in water and saline solutions.

Other monomers, which do not fall within the description of the monomers described above may be employed in minor amounts, that is up to about 8% by weight, provided they do not adversely affect the basic and novel characteristics of the polymers of this invention. For example, acrylamide, 2-ethylhexyl acrylate, hydroxyethyl acrylate and hydroxyethyl methacrylate may be employed as partial replacement for methyl acrylate or ethyl acrylate, and itaconic acid, maleic acid or maleic anhydride employed as partial replacement for methacrylic acid or acrylic acid.

The crosslinking technique used in the invention to transform water-soluble polymers into insoluble, water-swellable salt polymers is well known as free radical addition polymerization. Crosslinking agents usable according to the invention are polyunsaturated polymerizable vinyl monomers containing two or more free radical polymerizable ethylenic groups. Substantially any monomer having more than one polymerizable ethylene group can be used which monomer must be able to enter into vinyl addition polymerization reactions with the foregoing mentioned acids and acrylates. Illustrative examples include:

(1) diacrylate esters and dimethacrylate esters of glycols such as ethylene glycol dimethacrylate, propylene glycol dimethylacrylate, butylene glycol dimethacrylate and hexylene glycol dimethacrylate;

(2) diacrylate esters and dimethacrylate esters of ether or polyether glycols such as diethylene glycol diacrylate, diethylene glycol dimethacrylate, triethylene or tetraethylene glycol diacrylate and triethylene or tetraethylene glycol dimethacrylate;

(3) allyl esters of polymerizable unsaturated carboxylic acids such as allyl acrylate, methallyl acrylate, allyl methacrylate, allyl ethacrylate, ethallyl acrylate, methallyl methacrylate;

(4) di or trivinyl aromatic compounds such as divinyl benzene, and trivinyl benzene;

(5) di or triallyl esters of di and tribasic acids such as diallyl phthalate, triallyl cyanurate, diallyl maleate, diallyl succinate, triallyl phosphate, diallyl oxalate, diallyl malonate, diallyl citrate, diallyl fumarate, diallyl ether; and (6) acrylate or methacrylate esters of polyols such as di or triacrylate or methacrylate esters of trimethylol ethane, trimethylol propane or pentaerythritol.

In order to achieve the desired polymer properties, it is important that the monomers be polymerized together in certain specified proportions, although the exact proportions will vary depending on the polymer characteristics desired. The olefinically-unsaturated carboxylic acids of the invention are employed in amounts of from about 15% to about 50% by weight and most preferably from about 20% to about 40% by weight, based on the total weight of the monomers used. If the amount of carboxylic acid employed exceeds about 50% by weight, the resulting polymer salt becomes excessively hydrophilic while absorbing excessive amounts of water leading to a (1) soluble polymer, (2) viscous solution or suspension, and (3) loss of polymeric structural integrity. If the amount of carboxylic acid is less than about 15%, the resulting polymer salt is insufficiently hydrophilic and exhibits poor water absorption.

The alkyl acrylates are employed in amounts of about 49.07% to about 82% by weight and most preferably from about 59.02% to about 78% by weight, based on the total weight of the monomers used. If the amount of the acrylate employed exceeds about 82% by weight, then the resulting polymer in salt form is insufficiently hydrophilic and exhibits poor water absorption. If the amount of acrylate is less than about 49.07%, the resulting polymer becomes excessively hydrophilic while absorbing excessive amounts of water leading to a (1) soluble polymer, (2) viscous solution or suspension, and (3) loss of polymeric structural integrity.

The amount of crosslinking agent employed is desirably limited to an amount from about 0.03% to about 3.0% by weight, preferably from about 0.08% to about 2.0%. This low amount of crosslinking agent has been found sufficient to render the polymer salt water-insoluble while retaining a high degree of water absorbency. Use of less than 0.03% results in a polymer which upon neutralization functions primarily as a thickening agent lacking discrete particle identity. As the amount of crosslinking agent is increased above 0.03%, the more discrete and rigid the resulting polymer becomes rendering expansion of the salt particles less possible. Water absorbency drops to a commercially unacceptable level when amounts greater than 3.0% crosslinking agent are used.

The preferred polymer is prepared from a mixture containing as essential ingredients from about 20% to about 40% by weight of an olefinically-unsaturated carboxylic acid selected from methacrylic acid and acrylic acid; from about 59.02% to about 78% by weight of an alkyl acrylate selected from methyl acrylate, ethyl acrylate and n-butyl acrylate, and from about 0.08% to about 2.0% by weight of a crosslinking agent.

The polymeric constituents should be reacted as completely as possible during polymerization. The polymer may be made by conventional polymerization techniques such as by solution, suspension or emulsion polymerization on a batch, continuous or semi-continuous basis.

Suspension polymerization is preferred since this technique results in an acid polymer product as a high surface area granular precipitate having an average particle size between 50 and 400 microns, which product appears to be composed of accretions of smaller particles in the 10 to 50 micron range. A large proportion of these smaller particles appear as high surface area donuts of collapsed spherical shapes with 2 to 5 micron protuberances on their surfaces.

The polymerization reaction is carried out in the presence of a catalyst. The catalysts which form free radicals necessary for the reaction are conventional and are usually organic peroxides, inorganic persulfates and free radical generating azo compounds. The amount of catalyst used is normally from about 0.01 to about 2.0 parts by weight per 100 parts by weight of the total monomeric material to be reacted. Representative examples of organic peroxides include benzoyl peroxide, acetyl peroxide, bis(p-bromobenzoyl)peroxide, di-t butyl peroxide, t-butyl hydroperoxide, dicumyl peroxide, cumene hydroperoxide, bis(p-methoxybenzoyl)-peroxide, 2,2'-azobisisobutyronitrile and the like. Exemplary inorganic persulfates include ammonium, sodium and potassium persulfates. These may be used alone or in conjunction with sodium or potassium bisulfite. While polymerization is preferably carried out with a free radical catalyst, radiation induced polymerization can also be employed such as high energy X-rays or gamma rays.

Suitable conventionally employed surface active agents and/or colloids may also be used during the polymerization reactions.

Polymerization times, and temperatures may vary considerably depending on the monomer system and catalyst used. The polymerization reaction will generally be completed within at least 30 minutes to several hours at temperatures from around 0° C. to 100° C. and preferably within 1 to 4 hours at 65° C. to 90° C. for maximum efficiency.

In the preferred embodiment suspension polymerization is conducted in the following manner. A reactor is charged with deionized water and a suspension agent and deaerated with an inert gas. The reactor may be optionally heated to dissolve the suspension agent. Previously determined amounts of olefinically-unsaturated carboxylic acid and alkyl acrylate are added either separately or in admixture. Addition may occur at room temperature or at the reaction temperature. The crosslinking agent and catalyst may be added simultaneously with the monomer mixture or separately.

The reactor contents are then agitated by conventional means and heated to commence polymerization at a temperature around the lowest boiling point of the monomers. When methyl acrylate is polymerized, this temperature is about 70° C. The reaction is then allowed to continue to polymerize to completion whereupon the reactor contents are cooled. The polymer product may be alternately recovered from the slurry by conventional filtration means or directly converted in the slurry to its salt form. The final product slurry can be steam-treated at about 100° C. to remove any traces of unreacted monomers. Alternately, a highly reactive redox catalyst is added to essentially provide a 100% yield. The slurry can then be filtered to recover the polymer in its nonswelling acid form or neutralized by adding to the final slurry calculated amounts of an aqueous alkaline solution to convert the free acid groups to the salt form. Alternatively, the filtered polymer cake may be redispersed in water and neutralized as above or dried, pulverized and then neutralized with alkali.

Typically the solids content of the final reaction mixture is from about 15% to about 50%. Lower solid contents can be used but are generally undesirable from an economic standpoint.

The resulting polymer products in dried or slurry form may then be stored or used directly in an absorbent article such as by treating a substrate. For example, the article which may be a substrate is treated with the acid polymer which is then neutralized with an alkaline solution to form a water-swellable polymer by conventional neutralization methods. It is to be understood for the purpose of this invention that the treating step implies a complete particle dispersion on the substrate or discontinuous dispersion. The substrates to be treated may vary widely depending on the end use but include fibrous substrates such as wood pulp, cellulose batting, paper, woven or non-woven cloth and the like.

Any suitable organic or inorganic base may be used during neutralization. Representative compounds include sodium hydroxide, potassium hydroxide, lithium hydroxide, ammonium hydroxide, ammonia, and sodium carbonate. Neutralization may also be achieved with organic amines such as ethanolamine, diethanolamine, triethanolamine, methyl diethanolamine, butyl diethanolamine, diethyl amine, dimethyl amine, trimethyl amine, triethyl amine, tributyl amine, and so forth, and mixtures thereof. The most preferred base is sodium hydroxide. In short, any basic material may be used which does not adversely affect the polymer composition.

It is critical in the process of the invention, and particularly during neutralization reaction to employ the minimum quantity of water required to effect complete and uniform reaction and neutralization. Effective amounts of water usable in the invention have been found to range from a weight ratio of about 4 to 10:1 and preferably about 5 to 7:1 for total water to polymer ratio. When a ratio of less than 4:1 is employed, there is a danger that all of the free water will be rapidly absorbed during neutralization by only a portion of the acid polymer as it is neutralized leaving little if any water to conduct the remaining neutralizing agent to unneutralized acid polymer particles. On the other hand, a ratio above 10:1 results in excessive energy expenditures during drying to remove the unnecessary large amount of absorbed water.

In order to effect complete neutralization, stoichiometry should be observed between the equivalents of base dissolved in the alkaline neutralizing solution and the carboxylic acid equivalents in the polymer slurry. Thus, at least one equivalent of base, such as sodium hydroxide, per equivalent of carboxylic acid containing monomer moiety should be employed. However, as much as a 20 equivalent percent excess of base may be employed to insure that all the carboxylic acid groups are reached by the neutralizing solution. In fact, a slight excess is desirable to drive the reaction and achieve maximum swelling. This excess alkalinity is not harmful since it reacts upon drying by partially saponifying the acrylate ester segments, particularly the methyl acrylate, to yield additional sodium acrylate monomer units in the polymer chain backbone.

Drying of the polymer salt may be done by conventional means such as fluid bed drying, rotary kiln drying, tray drying, vacuum drying and oven drying, at sufficient temperatures to remove essentially all of the water associated with the polymer product without resulting in polymer decomposition. Products containing up to 5% residual absorbed water are acceptable materials. Preferred drying temperatures may be between 25° C. and 150° C. and most preferably between 80° C. and 100° C.

During drying, the polymer salt particles become agglomerated forming a friable mass of solid particles. This mass may be ground to form discrete particles for ease of handling and shipping. Depending on the particular end use desired, it has been found that particles between about 50 microns and about 2 millimeters result in a particle that rapidly absorbs water and enables water to pass a mass of previously swollen particles to reach as yet untouched material. It should be recognized that as particle size increases the particle surface area to volume decreases which results in slower water absorption and ultimately larger swelled particles. Likewise, small particle size material when used in bulk tend to absorb water at a slower rate than larger particles as a result of decreased interparticle pore size and accordingly decreased percolation rate.

The polymer product of the invention has an indeterminate "weight average" molecular weight because of its crosslinking and insolubility in solvents commonly used in the determination of molecular weights. The neutralized polymer is capable of absorbing surrounding water many times its own weight. In doing so, each individual absorbent particle swells or enlarges several times its individual diameter without destruction of the particles' particulate integrity. Absorption of distilled water in amounts greater than 100×weight have been noted. In 1% sodium chloride solutions up to 30×weight increases have occurred whereas in 15% to 25% sodium chloride solutions up to 10×weight increases have been noted. This amount of absorption is significant, especially when it is recognized that the polymer particle substantially immobilizes the same therein and the resulting particulate material retains its structure integrity.

The water-insoluble, water-swellable polymer of this invention is preferably used in an absorbent dressing or article of manufacture requiring water retention ability.

The polymer material when used in the foregoing applications is preferably in solid, granular form to provide the largest surface area for absorption and insure that maximum surface area is available for absorbency. There should be at least about 1% by weight, with possibly up to 90% by weight of the polymer salt present in the absorbent articles based on the total weight of the composite absorbent article.

Depending upon the specific kind of absorbent article, the polymer salt may be dispersed on a carrier sheet or flexible support comprising an absorbent layer of textile fibers, wood pulp fibers, cotton linters and the like as well as mixtures thereof. Such absorbent layers may be those which are commonly used in making absorbent dressings, and articles of manufacture discussed above such as surgical and dental sponges, catamenial tampons, diapers, meat trays, household pet litter mats, water separation devices such as filter cores, and the like. These materials may contain multiple layers of carrier sheets or supports and outer covering sheets all well known in the art.

Such absorbent articles may be prepared when the polymeric material is incorporated into the absorbent dressing by conventional procedures according to the invention, thus insuring that the desired particulate polymer is maintained in the final structure. In the case of a catamenial tampon, this can be accomplished by spreading the polymer particles as a layer over a layer of absorbent fibers and then winding the layer into the form of a roll so the polymer particles are entrapped therein. Steaming and drying the composite will increase the adhesion of the particles to the fibers. The resultant absorbent material will maintain its particular character as it absorbs water. Other well known methods for preparing such articles are contemplated to be within the scope of the invention.

The water-insoluble, water-swellable polymers of this invention may also be used as a soil modifier to improve water retention and increase air capacity. When blended with soils of varying sand-silt-clay compositions and particularly with high sand contents, significantly improved water retaining capacity is noted. The higher water retaining capacity is observed even at pressures from 1 to 15 bars.

Use of the polymer salts are clearly superior to untreated control soils, the effect being most significantly seen in the sandier more porous soils. Such soils characteristically lose excessive amounts of water through both evaporation and drainage and the polymers strongly counteract this effect. A concomitant effect of excessive drainage in sandy soils is the loss of nutrients through wash out. The inventive polymers likewise counteract this effect so that nutrients added to the soil are retained for longer periods of time.

In view of the outstanding water retention properties of these polymers, they are especially suited for use in preventing wilting of plants grown in sandy, free draining soils such as are found in the arid regions of the earth. They are beneficial in maintaining plant viability during periods of drought and are particularly useful in turfs constructed of sand or free draining sandy soils such as are used in golf greens, athletic arenas and walks. They are also useful in nurseries, greenhouses, home gardens, in artificial soils and in potted plants. The expense and need for constant watering and surveilance is substantially reduced. Thus, they ease water management burdens by holding more water in a plant bed and reduce the amount of field irrigation or greenhouse watering thus saving labor. They will also improve marginal lands by increasiing water holding capabilities of soils making them suitable for crop production. Finally, they are useful in loosening soils which have been compacted by natural or manmade processes such as grassed or bare pathways, plow pans or fragipans. They are also useful in transplants where the water retention properties and the close contact between the root tendrils and the water swollen polymer particles reduces transplant shock and loss of plant stock. A further use of this polymer is in seed coats which provide a water rich, drought resistant environment for germination and initial stages of growth.

When used in soils, the preferred polymer material is the sodium salt of 65/35/0.1 EA/MAA/EGDMA. While generally not equal to the sodium salt in terms of water retention properties, the potassium salt offers an advantage in supplying a nutrient which is not easily washed out and is available to the plant over an extended growing period. This is due to the fact that the potassium in the form of the counter ion to the polymer is only slowly released in comparison to the solubilization rate of typical soluble synthetic potassium containing fertilizers. Potassium fertilization and water retention can thus be optimized by utilizing blends of both sodium and potassium polymer salts.

As used herein, the term soil refers to any medium in which plants can be grown and which provides a means for support, oxygen, water and nutrients. Exemplary materials include natural growth media and artificial or unnatural growth media such as glass beads, foamed organic materials such as foamed polystyrene or polyurethane, calcined clay particles, comminuted plastic and the like.

The following examples are given to further illustrate the invention but are not deemed to be limiting thereof. All parts and percentages given are based upon total weight unless otherwise indicated.

The following procedure is employed in the examples where applicable to determine water and saline solution absorption. Add one gram of the polymer salt to 100 grams of a 1% NaCl solution or 200 grams distilled water. Allow to stand without agitation for two hours. Filter the material using a Whatman No. 4 filter paper until no water passes through (usually 5 to 15 minutes). Weigh the swollen product, subtract the weight of the polymer, i.e. one gram, and repor the results as swelling value. The rate of absorption is determined by adding one gram of the polymer salt into 30 grams distilled water in a small jar. The contents of the jar are stirred gently by shaking. The time necessary for the polymer to turn completely solid, that is, the product does not flow freely when the jar is inverted, is observed and recorded.

EXAMPLE I

This Example illustrates a method for preparing the polymers of this invention by the preferred suspension polymerization technique.

A polymerization reactor was charged with 2,000 grams of deionized water and 3 grams of Cellosize QP-4400 (product of Union Carbide which is a hydroxyethyl cellulose powder having a 2% viscosity of 4,000 to 6,000 cps) as a suspending agent. The contents of the reactor were heated to 65° C. until the hydroxyethyl cellulose dissolves and then cooled to 35° C.

To the reactor was then added with agitation, a mixture containing 325 grams methyl acrylate, 175 grams glacial methacrylic acid, 0.5 grams ethylene glycol dimethacrylate as crosslinking agent and 0.5 grams azobisisobutyronitrile as catalyst. The contents of the reactor were deaerated by purging with nitrogen which is passed therethrough at a moderate flow rate (e.g., 100 milliliters per minute). The temperature was raised to 70° C. and the mixture allowed to polymerize for three hours. In the last hour the reactor temperature was raised to 80° C. to complete the reaction. The total reaction time was three hours. The contents of the reactor was continuously agitated during the entire polymerization reaction.

Upon completion of the reaction, the reactor slurry was cooled to 25° C. and filtered by passing the slurry through a vacuum filter. The filter cake weighed 1,000 grams. To analyze the product and determine yield, a one-fifth portion of the filter cake is dried for 16 hours in a vacuum oven at 80° C. and ground to an average 40 mesh size (U.S. Standard Sieve size) to prepare a granular acid polymer containing approximately 34 to 36% methacrylic acid. The percent conversion of monomers to polymer product was 97.0%.

The remaining portions of the filter cake were neutralized with a basic solution of sodium hydroxide by separately dispersing each remaining one-fifth portion of the cake in 400 grams of deionized water followed by rapid and complete addition of 195 grams of a 10% sodium hydroxide solution (e.g., a 20% excess over the theoretical amount necessary to neutralize the polymer). The resulting masses were dried at 80° C. in a vacuum oven to remove contained water and then ground to a size to pass through a 20 mesh screen, U.S. Standard Sieve size.

The saline absorbency of the polymer salt was determined in a 1% sodium chloride solution. The filter cake weighed 24 grams which corresponds to a water pickup of 23 times its own weight. In the water absorbency test, water pickup of about 100 times the weight of the polymer was achieved.

EXAMPLES 2 TO 17

Examples 2 to 17 prepare polymers by the suspension polymerization technique of Example 1 using different weight ratios of methyl acrylate (MA), methacrylic acid (MAA), and ethylene glycol dimethacrylate (EDMA) as crosslinking agent in the amounts as set forth in Table 1. The polymers of Examples 2 to 12 were neutralized according to the process of Example 1 except that a lithium hydroxide solution was used in lieu of the sodium hydroxide solution. The procedure of Example 1 was used for neutralizing the acid polymers of Examples 13 to 17.

In Table I, the absorbency capacity of the alkaline polymers is set forth in amounts times the dry weight of the polymer. Absorbency values are given for deionized water, a 15% calcium chloride solution and a 15% sodium chloride solution. For convenience of computation, the recited amounts of crosslinking agent represent that amount of material added to the other two monomers used.

The results clearly indicate that the polymers of this invention have a high absorbency capability for water and saline solutions over a wide range of monomer and crosslinking aggent concentrations. The data also shows that water pickup decreases as the crosslinking agent level increases. Products obtained having about 95% water absorption content consisted of hard swollen particles retaining structural integrity which are dry to the touch. At higher water absorption levels the swollen particles are slightly softer but are discrete and nonagglomerated particles being semi-dry to the touch.

are sensitive to high CaCl$_2$ and NaCl concentrations, the polymers still maintain a high level of absorbency while retaining structural integrity. Example 24 also demonstrates the utility of a polymer having a portion of the carboxylic acid monomer replaced with a minor amount of a different acid monomer.

TABLE II

| Example | Carboxylic Acid Monomer (parts) | Alkylacrylate Monomer (parts) | Crosslinking Agent (parts) | Absorption Times Dry Weight | | | |
|---|---|---|---|---|---|---|---|
| | | | | Water | 1% NaCl | 15% NaCl | 15% CaCl$_2$ |
| 18 | 20 MAA | 80 EA | 2 EDMA | 11 | NT | NT | 0.8 |
| 19 | 35 MAA | 65 EA | 0.1 EDMA | NT | 31 | NT | NT |
| 20 | 20 AA | 80 MA | 1 EDMA | 19 | NT | NT | 2.6 |
| 21 | 20 AA | 80 MA | 0.5 EDMA | 22 | NT | 2.3 | 1.5 |
| 22 | 35 AA | 65 MA | 0.1 EDMA | NT | 20 | NT | NT |
| 23 | 35 MAA | 65 BA | 0.1 EDMA | NT | 20 | NT | NT |
| 24 | 25.8 MAA + 5.8 M | 65 MA | 0.1 EDMA | NT | 21 | NT | NT |

MAA = methacrylic acid
AA = acrylic acid
M = maleic acid
EA = ethyl acrylate
MA = methyl acrylate
BA = butyl acrylate
EDMA = ethylene glycol dimethacrylate
NT = not tested

TABLE I

| Example | MA | MAA | EDMA | Absorption Times Dry Weight | | |
|---|---|---|---|---|---|---|
| | | | | Water | 15% CaCl$_2$ | 15% NaCl |
| 2 | 80 | 20 | 2 | 11 | 2 | NT |
| 3 | 80 | 20 | 1 | 18 | 3.2 | 4.8 |
| 4 | 80 | 20 | 0.5 | 22 | 4.9 | 5.5 |
| 5 | 75 | 25 | 1 | 18 | 4.8 | 6.9 |
| 6 | 70 | 30 | 1 | 17 | 5.5 | 6.3 |
| 7 | 60 | 40 | 1 | 16 | 4.8 | NT |
| 8 | 85 | 15 | 1 | 13 | 1.8 | NT |
| 9 | 75 | 25 | 0.5 | 28 | 5.8 | 6.9 |
| 10 | 75 | 25 | 0.3 | 37 | 6.1 | 8.6 |
| 11 | 75 | 25 | 0.2 | 44 | 5.3 | 8.4 |
| 12 | 75 | 25 | 0.1 | 60 | 8.1 | 10.9 |
| 13 | 70 | 30 | 1 | 17 | 5.5 | 6.3 |
| 14 | 70 | 30 | 0.5 | 31 | 6.2 | 7.8 |
| 15 | 70 | 30 | 0.3 | 57 | 7.7 | 10.1 |
| 16 | 70 | 30 | 0.1 | 86 | 9.1 | 13.0 |
| 17 | 70 | 30 | 0.05 | 105 | 8.6 | 13.0 |

MA = methyl acrylate
MAA = methacrylic acid
EDMA = ethylene glycol dimethacrylate

EXAMPLES 18 TO 24

Examples 18 to 24 demonstrate the preparation of polymers according to the procedure of Example 1 using different weight ratios of various monomers. The polymers of Examples 18, 20 and 21 were neutralized according to the process of Example 1 except that a lithium hydroxide solution was used in lieu of the sodium hydroxide solution. Examples 19 and 22 to 24 employed the neutralization process of Example 1 with sodium hydroxide. The amounts of polymer components used and absorbency test results are recited in Table II. For convenience of computation, the recited amounts of crosslinking agent represent that amount of material added to the other monomers used.

The results indicate that acrylic acid yields approximately equivalent results as methacrylic acid in swelling in water. For swelling in the presence of high electrolyte concentrations, the methacrylic acid is preferred. While the results indicate that all of the polymers tested

EXAMPLES 25 and 26

Examples 25 and 26 used polymers prepared by the suspension polymerization technique of Example 1 using different weight ratios of monomers and crosslinking agents. The acid polymers were neutralized with basic solutions prepared from lithium hydroxide, sodium hydroxide, potassium hydroxide and triethanolamine. The monomers employed are methyl acrylate (MA), methacrylic acid (MAA), and ethylene dimethacrylate (EDMA). The amounts of monomers employed and the results are set forth in Table III. The amount of crosslinking agent represents that amount added to the two other monomers used.

The results demonstrate the effect of varying the neutralization agent and accordingly the resultant polymer salt product. The results indicate that sodium and lithium polymers have essentially equal absorption in water although the lithium compound exhibits superior results in electrolytic solutions. The potassium polymer exhibits lower swelling efficiency although it has particular use in agricultural applications because of its potential nutrient value. The triethanolamine salts are still lower in absorption capacity, yet would be quite useful in cosmetic applications.

TABLE III

| Example | MA | MAA | EDMA | Salt | Absorption Times Dry Weight | |
|---|---|---|---|---|---|---|
| | | | | | Water | 3.5% CaCl$_2$ |
| 25 | 80 | 20 | 2 | Li | 11 | 3.2 |
| | | | | Na | 12.4 | 2 |
| | | | | K | 9 | 1.8 |
| | | | | TEA | 5 | 1.3 |
| 26 | 80 | 20 | 1 | Na | 16 | 2.3 |
| | | | | Li | 18 | 3.2 |

EXAMPLES 27 TO 40

This example demonstrates the effect of varying the amount of polymer components to prepare water-swellable, water-insoluble polymers. The procedure of Example 1 was repeated to prepare the polymer-sodium salt. The amounts of monomers used and results are set forth in Table IV.

A single system consisting of methyl acrylate, methacrylic acid and ethylene dimethacrylate (MA/MAA/EDMA) was studied over an MA range of 50 to 80, MAA from 20 to 50, and EDMA from 0.03 to 0.3. The results indicate that for each crosslinking level maximum swelling in 1% NaCl was obtained with polymers around 35–40% MAA. The polymer particles which gave swollen particles of highest structural integrity were found within the MAA concentration range of about 20 to 40%. Beyond 50% MAA, and within the 0.3–0.03 crosslinking range, structural integrity of the swollen particle was lost. Structural integrity was likewise degraded at less than 0.03 crosslinking so that the neutralized polymer in water gave undefined, unfilterable particles which were indistinguishable from the gelled viscous slurries or solutions of the prior art.

TABLE IV

| Example | MA | MAA | EDMA | Absorption of 1% NaCl Times Dry Weight |
|---|---|---|---|---|
| 27 | 80 | 20 | 0.3 | 5 |
| 28 | 75 | 25 | 0.3 | 8.5 |
| 29 | 65 | 35 | 0.3 | 8.7 |
| 30 | 50 | 50 | 0.3 | 8.7 |
| 31 | 75 | 25 | 0.1 | 17 |
| 32 | 65 | 35 | 0.1 | 20.5 |
| 33 | 60 | 40 | 0.1 | 20 |
| 34 | 50 | 50 | 0.1 | 17.5 |
| 35 | 75 | 25 | 0.05 | 18 |
| 36 | 70 | 30 | 0.05 | 24 |
| 37 | 50 | 50 | 0.05 | 25 |
| 38 | 80 | 20 | 0.03 | 17 |
| 39 | 65 | 35 | 0.03 | 32.5 |
| 40 | 50 | 50 | 0.03 | 26.5 |

MA = methyl acrylate
MAA = methacrylic acid
EDMA = ethylene glycol dimethacrylate

EXAMPLES 41 TO 46

Examples 41 to 46 prepare polymers by the suspension polymerization technique of Example 1 using methyl acrylate and methacrylic acid with various amounts of different crosslinking agents. The results are set forth in Table V.

The results indicate that the polymer prepared with diethylene glycol dimethacrylate at 0.1% and 0.05% gives swelling ratios in 1% NaCl of 25 and 34X, respectively. Thus, the lower the crosslinking level gives the more easily hydratable and expandable polymer. The useful lower limit is reached, however, at 0.03% because beyond that point the particles no longer expand to an equilibrium absorption level where the swollen particles maintain their structural integrity, but rather absorb so much water that the structural integrity is lost. In the latter instance, the particles become very soft, fuse together and eventually give a viscous gel or even a viscous polymer solution. Extending beyond diethylene glycol dimethacrylate, higher glycols such as tetraethylene glycol, as its dimethacrylate derivative, has been used to increase the hydrophilicity of the crosslinking unit. Allyl methacrylate is an example of a crosslinking agent where one vinyl group is in the alkyl group of an acrylate ester and the second is in the carboxylate group, i.e., the methacrylate group. Divinyl benzene is an example of a hydrocarbon crosslinking agent containing no hydrolyzable ester groups and, accordingly, the resulting polymer is structurally completed with hydrolytically stable carbon-carbon links throughout its backbone and crosslink bridges.

TABLE V

| Example | MA | MAA | X-linker | | Absorption of 1% NaCl Times Dry Weight |
|---|---|---|---|---|---|
| 41 | 65 | 35 | 0.1 | diethylene glycol dimethacrylate | 25 |
| 42 | 65 | 35 | 0.05 | diethylene glycol dimethacrylate | 34 |
| 43 | 65 | 35 | 0.1 | trimethylol propane trimethacrylate | 23.5 |
| 44 | 65 | 35 | 0.1 | allyl methacrylate | 21 |
| 45 | 65 | 35 | 0.2 | tetraethylene glycol dimethacrylate | 18 |
| 46 | 65 | 35 | 0.1 | divinylbenzene | 23 |

MA = methyl acrylate
MAA = methacrylate acid

EXAMPLE 47

This example illustrates a method for preparing the polymers of this invention and neutralizing the polymer slurry in the presence of various surfactants.

A polymerization reactor was charged with 2,000 grams of deionized water and 3 grams of Cellosize QP-4400 (product of Union Carbide whichis a hydroxyethyl cellulose powder having a 2% viscosity of 4,000 to 6,000 cps) as a suspending agent. The contents of the reactor were heated to 65° C. until the hydroxyethyl cellulose dissolves and then cooled to 35° C.

To the reactor was then added with agitation, a mixture containing 325 grams methyl acrylate, 175 grams glacial methacrylic acid, 0.5 grams ethylene glycol dimethylacrylate as crosslinking agent and 0.5 grams azobisisobutyronitrile as catalyst. The contents of the reactor were then deaerated by purging with nitrogen which is passed therethrough at a moderate flow rate (e.g., 100 millimeters per minute). The temperature was raised to 70° C. and the mixture allowed to polymerize for three hours. In the last hour the reactor temperature was raised to 80° C. to complete the reaction. The total reaction time was three hours. The contents of the reactor was continuously agitated during the entire polymerization reaction.

Upon completion of the reaction, the reactor slurry was cooled to 25° C. The slurry was diluted with 500 grams water in order to allow better agitation and flow.

One-fifth aliquot portion (600 grams) of the slurry was transferred to a steel beaker and agitated very rapidly (3000 RPM) with a dispersator. To this was added 5% Aerosol OT as a surfactant (a dioctyl sodium sulfosuccinate from American Cyanamid). To the suspension was then added 195 grams of 10% NaOH and the slurry solidified at once into a soft swollen, friable, granular mass. The weight ratio of water to polymer in the neutralization step was 6.76 to 1. The friable solid sodium polymer salt was then dried at 80° C. in a vacuum oven to remove contained water and then ground to a size to pass through a 20 mesh screen, U.S. Standard Seive size. The resulting dried product absorbed 100 times its weight in water. In a 1% NaCl solution, 21 times its weight was absorbed. The rates of absorption were 8 seconds and 21 seconds, respectively.

EXAMPLE 48

This Example demonstrates the preparation of various absorbent articles with the polymers of this invention.

A. 0.5 Grams of finely ground dry polymer salt from Example 1 was added slowly to a 250-gram slurry of difiberized cellulose containing 5 grams cellulose. After mixing for 2 minutes, the slurry was diluted in the headbox of a conventional Noble and Wood Laboratory Sheet Machine and formed into a 12"×12" handsheet dried and tested for water absorbency. The article contained 10% polymer salt. The dry paper absorbed 12 times its weight of water.

B. A polymer suspension, prepared according to Example 47 was diluted to 15% solids content and neutralized with 20 mole % excess of 10% NaOH solution. The neutralized polymer swelled and absorbed all of the water to form a solid, friable paste. This was then diluted with water to 0.5% solids. 100 Grams of the slurry was added to a 250-gram slurry of a beaten cellulose pulp containing 5 grams cellulose. This was also converted to a 12"×12" handsheet as discussed above and tested for water absorbency. The dry paper absorbed 6.6 times its weight of water.

C. Six sheets of 4"×10" pieces of paper toweling weighing 3.5 grams were layered upon one another in a stack and dusted evenly between the layers with 3.5 grams of finely ground polymer salt from Example 1. The resulting multilayered pad was sprayed with water mist until the weight increased to 20 grams. The wet pad was then dried at 80° C. to fuse the layers together. The pad was tightly rolled into an oblong shape, immersed in a 1% NaCl solution for a few minutes, and then pressed under 1.5 lbs./sq. in. pressure for 5 minutes to determine the extent of saline absorption. The pad absorbed 9 times its weight of 1% NaCl solution. A similar control towel processed as discussed without the polymer absorbed 3 times its weight of the saline solution.

COMPARATIVE EXAMPLES A TO G

This example compares the water and saline solution absorption rates of various commercially available water-swellable, water-insoluble polymer products with the dried polymer salt prepared according to Example 1. The polymers tested and their known chemical description and results are set forth in Table VI. The results indicate that the polymers of the invention are unexpectedly superior water-swellable, water-insoluble compositions.

In the example, comparative material A is identified commercially as AQUALON and is a product of Hercules Inc. Comparative material B is identified commercially as VITERRA-1 and is a product of Union Carbide Corporation. Comparative material C is identified commercially as VITERRA-2 and is a product of Union Carbide Corporation. Comparative material D is identified commercially as PERMASORB-10 and is a product of National Starch & Chemical Corporation. Comparative material E is identified commercially as PERMASORB-30 and is a product of National Starch & Chemical Corporation. Comparative material F is identified commercially as H-SPAN and is a product of General Mills Chemicals, Inc. The material is produced under license from the U.S. Department of Agriculture. Comparative material G is identified commercially as DOWFLAKE and is a product of Dow Chemical Company and prepared according to U.S. Pat. Nos. 3,980,663 and 3,993,616.

TABLE VI

| | Absorption Times Dry Weight | |
|---|---|---|
| | Water | 1% NaCl |
| Inventive Product | 100 | 21 |
| Comparative A fibers of internally crosslinked sodium carboxymethylcellulose | 16 | 5 |
| Comparative B crosslinked polyethylene oxide | 13 | — |
| Comparative C | Gelled mass. | Gelled mass. |
| acrylamide-Na acrylate copolymer | Cannot filter. | Cannot filter. |
| Comparative D | Gelled mass. | Gelled mass. |
| acrylic polymer with hydrophilic carboxylate | Cannot filter. | Cannot filter. |
| Comparative E acrylic polymer with hydrophilic carboxylate groups | Cannot filter. | 20.4 |
| Comparative F hydrolyzed starch polyacrylamide graft | Cannot filter. | Cannot filter. |
| Comparative G | Gelled mass. | Gelled mass. |
| crosslinked salt of linear carboxylic acid polyelectrolyte | Cannot filter. | Cannot filter. |

The invention being thus described, it will be obvious that the same may be varied in many ways. Such variations are not to be regarded as a departure from the spirit and scope of the invention, and all such modifications are intended to be included within the scope of the following claims.

We claim:

1. In an absorbent dressing comprising an absorbent layer containing a water-swellable, water-insoluble material, the improvement which comprises having at least a portion of the water-swellable, water-insoluble material being an alkaline salt of a polymer prepared by the reaction of (a) from about 15% to about 50% by weight of an olefinically-unsaturated carboxylic acid containing an activated carbon-to-carbon olefinic double bond and at least one carboxyl group;

(b) from about 49.07% to about 82% by weight of an alkyl acrylate wherein the alkyl group has from 1 to 6 carbon atoms; and (c) from about 0.03% to about 3.0% by weight of a crosslinking agent which are polyunsaturated polymerizable vinyl monomers containing two or more free radical polymerizable ethylenic groups, said crosslinking agent being introduced directly into the carbon-carbon backbone of the polymer; and having the formula:

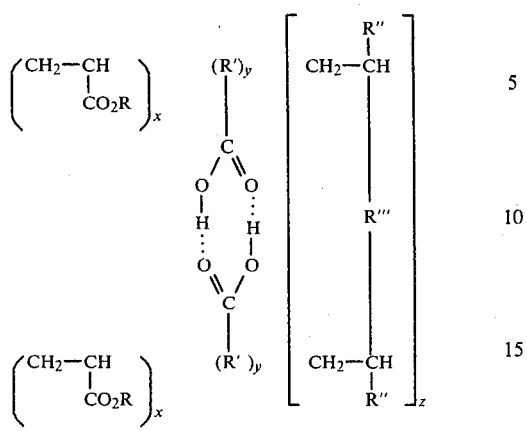

wherein:
- x represents the relative number of alkyl acrylate groups with R being 1 to 6 carbon atoms as component (b);
- y represents the relative number of olefinically-unsaturated carboxylic acid groups with R' being the hydrocarbon portion of the carboxylic acid compounds of component (a);
- z represents the relative number of crosslinking agents of component (c) with R" being hydrogen or methyl and R'" comprising the remaining portion of component (c).

2. The absorbent dressing of claim 1 comprising from about 20% to about 40% by weight of the olefinically-unsaturated carboxylic acid selected from the group consisting of methacrylic acid and acrylic acid.

3. The absorbent dressing of claim 1 wherein up to 8% by weight of the total amount of olefinically-unsaturated carboxylic acid present is replaced with a material selected from the group consisting of itaconic acid, maleic acid and maleic anhydride.

4. The absorbent dressing of claim 1 comprising from about 59.02% to about 78% by weight of the alkyl acrylate selected from the group consisting of methyl acrylate, ethyl acrylate and n-butyl acrylate.

5. The absorbent dressing of claim 1 comprising about 0.08% to about 2% by weight crosslinking agent.

6. As an article of manufacture, a flexible support adapted for the absorption of water, said support containing a solid, water-swellable, water-insoluble polymer, said polymer comprising the alkaline salt of a polymer prepared from the reaction of materials consisting essentially of
   (a) from about 15% to about 50% by weight of an olefinically-unsaturated carboxylic acid containing an activated carbon-to-carbon olefinic double bond and at least one carboxyl group;
   (b) from about 49.07% to about 82% by weight of an alkyl acrylate wherein the alkyl group has from 1 to 6 carbon atoms; and
   (c) from about 0.03% to about 3.0% by weight of a crosslinking agent which are polyunsaturated polymerizable vinyl monomers containing two or more free radical polymerizable ethylenic groups, said crosslinking agent being introduced directly into the carbon-carbon backbone of the polymer; and having the formula:

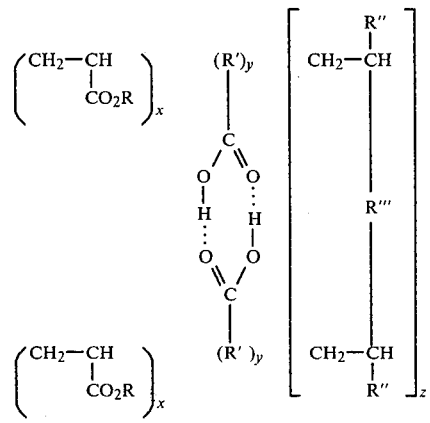

wherein:
- x represents the relative number of alkyl acrylate groups with R being 1 to 6 carbon atoms as component (b);
- y represents the relative number of olefinically-unsaturated carboxylic acid groups with R' being the hydrocarbon portion of the carboxylic acid compounds of component (a);
- z represents the relative number of crosslinking agents of component (c) with R" being hydrogen or methyl and R'" comprising the remaining portion of component (c).

7. The article of manufacture of claim 6 comprising from about 20% to about 40% by weight of the olefinically-unsaturated carboxylic acid selected from the group consisting of methacrylic acid and acrylic acid.

8. The article of manufacture of claim 6 wherein up to 8% by weight of the total amount of olefinically-unsaturated carboxylic acid present is replaced with a material selected from the group consisting of itaconic acid, maleic acid and maleic anhydride.

9. The article of manufacture of claim 6 comprising from 59.02% to about 78% by weight of the alkyl acrylate selected from the group consisting of methyl acrylate, ethyl acrylate and n-butyl acrylate.

10. The article of manufacture of claim 6 comprising about 0.08% to about 2% by weight crosslinking agent.

* * * * *